US00RE47478E

(19) United States
(12) Reissued Patent
Thompson

(10) Patent Number: US RE47,478 E
(45) Date of Reissued Patent: Jul. 2, 2019

(54) NATURAL GAS LIQUID PRESSURE REGULATING VAPORIZER SAMPLING SYSTEM

(71) Applicant: Mustang Sampling LLC, Ravenswood, WV (US)

(72) Inventor: Kenneth O. Thompson, Ravenswood, WV (US)

(73) Assignee: Mustang Sampling LLC, Ravenswood, WV (US)

(21) Appl. No.: 15/477,507

(22) Filed: Apr. 3, 2017

Related U.S. Patent Documents

Reissue of:
(64) Patent No.: 9,285,299
Issued: Mar. 15, 2016
Appl. No.: 13/829,029
Filed: Mar. 14, 2013

U.S. Applications:
(60) Provisional application No. 61/729,892, filed on Nov. 26, 2012.

(51) Int. Cl.
*G01N 1/10* (2006.01)
*G01N 1/22* (2006.01)

(52) U.S. Cl.
CPC ..... *G01N 1/2247* (2013.01); *G01N 2001/105* (2013.01); *G01N 2001/2238* (2013.01)

(58) Field of Classification Search
CPC ..... F17C 2221/033; F17C 2223/0161; F17C 2227/0393
USPC ..... 73/61.59, 863.11
See application file for complete search history.

(56) References Cited

U.S. PATENT DOCUMENTS

| | | | | |
|---|---|---|---|---|
| 3,421,336 | A * | 1/1969 | Lichtenberger | B60H 1/3202 62/239 |
| 6,464,101 | B1 * | 10/2002 | Siragusa | B62D 25/24 220/787 |
| 7,162,933 | B2 | 1/2007 | Thompson et al. | |
| 7,484,404 | B2 | 2/2009 | Thompson et al. | |
| 8,056,399 | B2 | 11/2011 | Thompson et al. | |
| 9,285,299 | B2 | 3/2016 | Thompson | |
| 2009/0151427 | A1 * | 6/2009 | Thompson | F17C 6/00 73/23.41 |
| 2009/0155642 | A1 * | 6/2009 | Popham | H01M 8/0612 429/411 |
| 2010/0012201 | A1 * | 1/2010 | Welker | F16K 15/028 137/535 |
| 2012/0048881 | A1 * | 3/2012 | Drube | F17C 7/02 62/50.1 |

(Continued)

OTHER PUBLICATIONS

"White Paper on Liquid Hydrocarbon Drop Out in Natural Gas Infrastructure," NGC+ Liquid Hydrocarbon Dropout Task Group, Feb. 28, 2005.

(Continued)

*Primary Examiner* — Kenneth Whittington
(74) *Attorney, Agent, or Firm* — Cahn & Samuels, LLP

(57) ABSTRACT

System and method for natural gas liquid sample pressure regulating vaporizer system including a vented cabinet having a gas sample input, a pressure regulator, a single path vaporizer, a liquid block, a heated regulator and a gas sample outlet, and a communications assembly including a temperature controller, a communication outlet, and a power input electrically connected via appropriate secure feedthroughs to the cabinet.

18 Claims, 4 Drawing Sheets

(56) References Cited

U.S. PATENT DOCUMENTS

| | | | | |
|---|---|---|---|---|
| 2012/0118566 | A1* | 5/2012 | Vandor | C09K 8/62 166/280.1 |
| 2012/0130359 | A1* | 5/2012 | Turovskiy | A61B 18/02 606/21 |
| 2012/0180556 | A1* | 7/2012 | Webster | G01N 21/643 73/61.43 |
| 2012/0222422 | A1* | 9/2012 | Nunley | C07C 67/055 60/645 |
| 2014/0137599 | A1* | 5/2014 | Oelfke | F25J 3/0209 62/619 |

OTHER PUBLICATIONS

Technical White Paper "Sample Liquid Petroleum Gas (and other high vapor pressure gas/liquids)", Sentry Equipment Corp, Tec1. 621 Rev. 0.

* cited by examiner

NATURAL GAS LIQUID PRESSURE REGULATING VAPORIZER SAMPLING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*RELATED APPLICATIONS*

*This application is a reissue of U.S. Pat. No. 9,285,299 originally filed as application Ser. No. 13/829,029 on Mar. 14, 2013 entitled NATURAL GAS LIQUID PRESSURE REGULATING VAPORIZER SAMPLING SYSTEM which claimed priority to Provisional Application Ser. No. 61/729,892 filed Nov. 26, 2012 and a patent term adjustment under 35 U.S.C. § 1154(b) extended by 332 days.*

FIELD OF INVENTION

This invention relates to collecting and conditioning samples from liquid natural gas inputs and, more particularly, to thermal conditioning of pipeline samples from a natural gas liquid source such as shale to maintain gas at a low pressure for analysis.

BACKGROUND

Gaseous NGL, not being cryogenic, tends to include considerable entrained liquid natural gas. The presence of such entrained liquids undermines the qualitative accuracy of the energy value of the measured gas. This problem has been exacerbated with the substantial development of shale gas obtained from fracking. Unlike the typical gas obtained from conventional sources, a new analytical complication has been introduced due to the presence of heavy hydrocarbons (e.g. those composed of more than five carbon atoms and generally in liquid form) not present in stream obtained from traditional gas wells. Because of the significantly increased presence of such "liquid heavies" at high pressures, gas energy analysis requires reliance on process gas chromatographs. Such equipment is expensive, large, complicated, and maintenance-intensive.

Therefore a need exists for improvement to the presently accepted and commonly used systems and methods of liquid natural gas sampling that rely on process gas chromatographs. Specifically, the need exists for a system permitting the use of standard gas chromatography equipment in NGL, and particularly shale gas, analysis.

SUMMARY OF INVENTION

It is an object of the present invention to provide a novel, liquid natural gas sampling system and method that overcomes the aforementioned problems associated with conventional structures and providing improved performance over the prior art.

Another object of the invention is to reduce the cost of equipment and labor associated with analysis of heavy hydrocarbon and liquid containing NGL.

Another object of the invention is to provide a system permitting NGL sampling and analysis using conventional gas chromatographic equipment. These and other objects are satisfied by a natural gas liquid sample vaporizer system comprising: a vented cabinet having a gas sample input, a pressure regulator, a single path vaporizer, a liquid block, a heated regulator and a gas sample outlet, and a communications assembly electrically connected via appropriate secure feedthroughs to the cabinet, said assembly including a temperature controller, a communication outlet, and a power input.

The invention relates generally to non-cryogenic liquid natural gas sample systems analysis systems. More specifically, the invention includes a system and method incorporating the use of a pressure regulator to reduce the incoming liquid pressure (e.g. 6000 psi for natural gas liquid) to a level not exceeding 200 psi. Without being bound to a particular theory, the invention adapts the behavior of pressure/temperature curve of liquid natural gas. Although somewhat counterintuitive, pressure reduction of the liquid gas sample also leads to a reduction of liquid temperature as represented by the curve illustrated in FIG. 4.

Immediately following pressure reduction, the low pressure liquid natural gas is introduced into a vaporizer which serves to eliminate the presence of any entrained liquid in the natural gas sample by heating the gas above the hydrocarbon dew-point temperature. For added confidence, the output from the vaporizer may be input into a heated liquid vapor filter/separator that is then passed to a single or multi-stage heated pressure regulator for output into the analyzer stream at an appropriate, reduced pressure. Where an in-line heated liquid filter and liquid block is employed, it is preferably associated with a purge drain for removal of any collected liquid that may incidentally have passed through the vaporizer prior to entry into the regulator.

In short the invention herein provides enhanced sample quality, through essentially, a three stage process involving controlled vaporization and remixing coupled with gas sample pressure reduction. The invention is designed to vaporize liquid while providing a fresh sample to a continuous online analyzer. More specifically, the invention is designed to first vaporize NGL, 2) remove any solids or liquids entrained with the gas, and 3) send a select sample to a heated regulator for pressure reduction that prevents hydrocarbon dew point dropout. Preferably, the invention is constructed as a single-path unit, combined with liquid blocking technology and a pre- and post-heated pressure regulator for hydrocarbon dew point dropout prevention. In this fashion, the pressure of the sample is reduced prior to delivery to a downstream, heated liquid block where the sample is substantially maintained in a stable condition. Because the invention eliminates post-vaporization hydrocarbon liquid dropout in a continuous gas flow facility, it is particularly useful for use in gas stripping facilities and where heavier hydrocarbon measurements are required.

For definitional purposes and as used herein "connected" includes physical, whether direct or indirect, permanently affixed or adjustably mounted, as for example, the vaporizer is connected to the pressure regulator. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION

Figure 1:
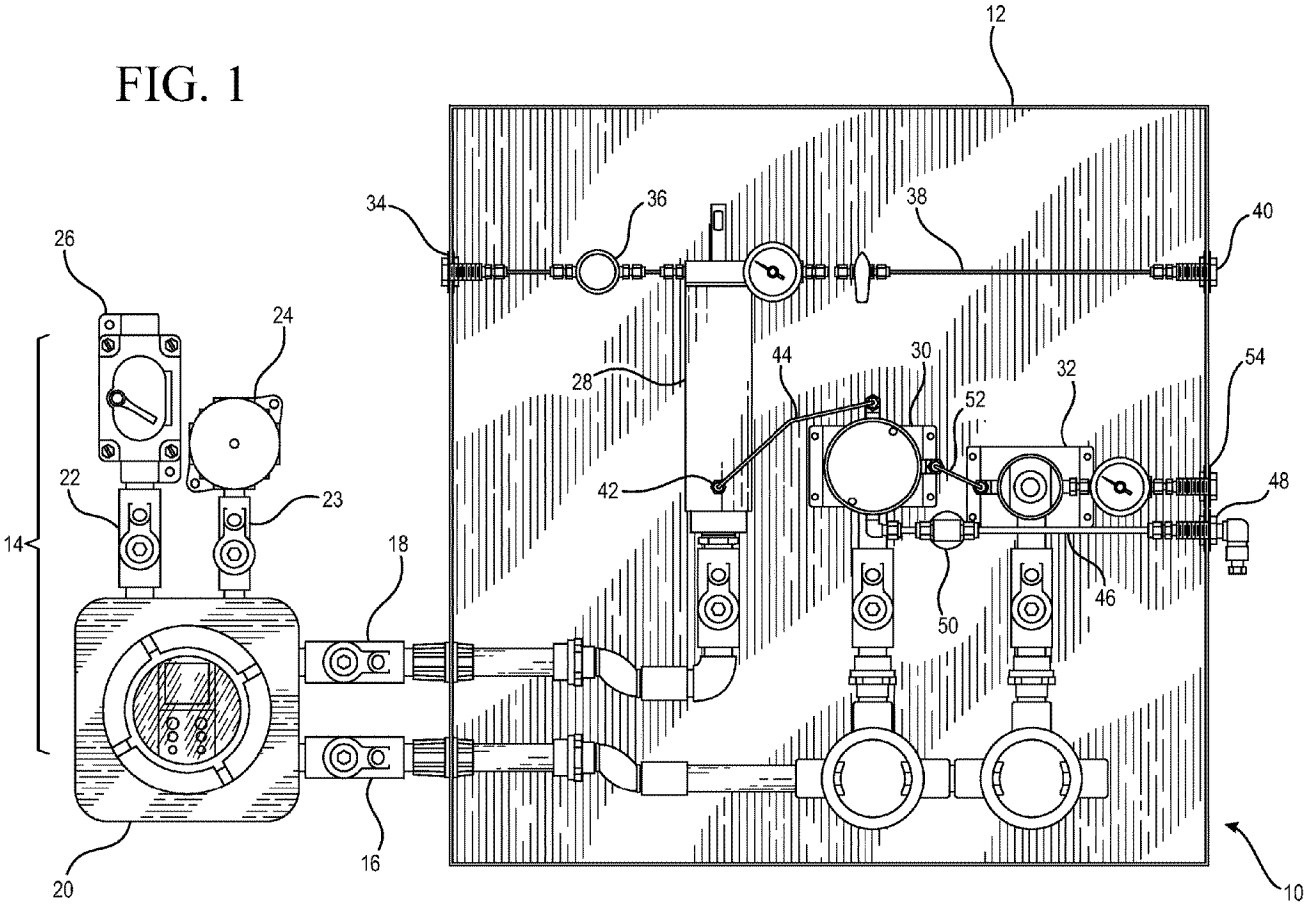
FIG. 1 is a labeled schematic of an embodiment of the natural gas liquid pressure regulating vaporizer system according to the invention.
Figure 2:
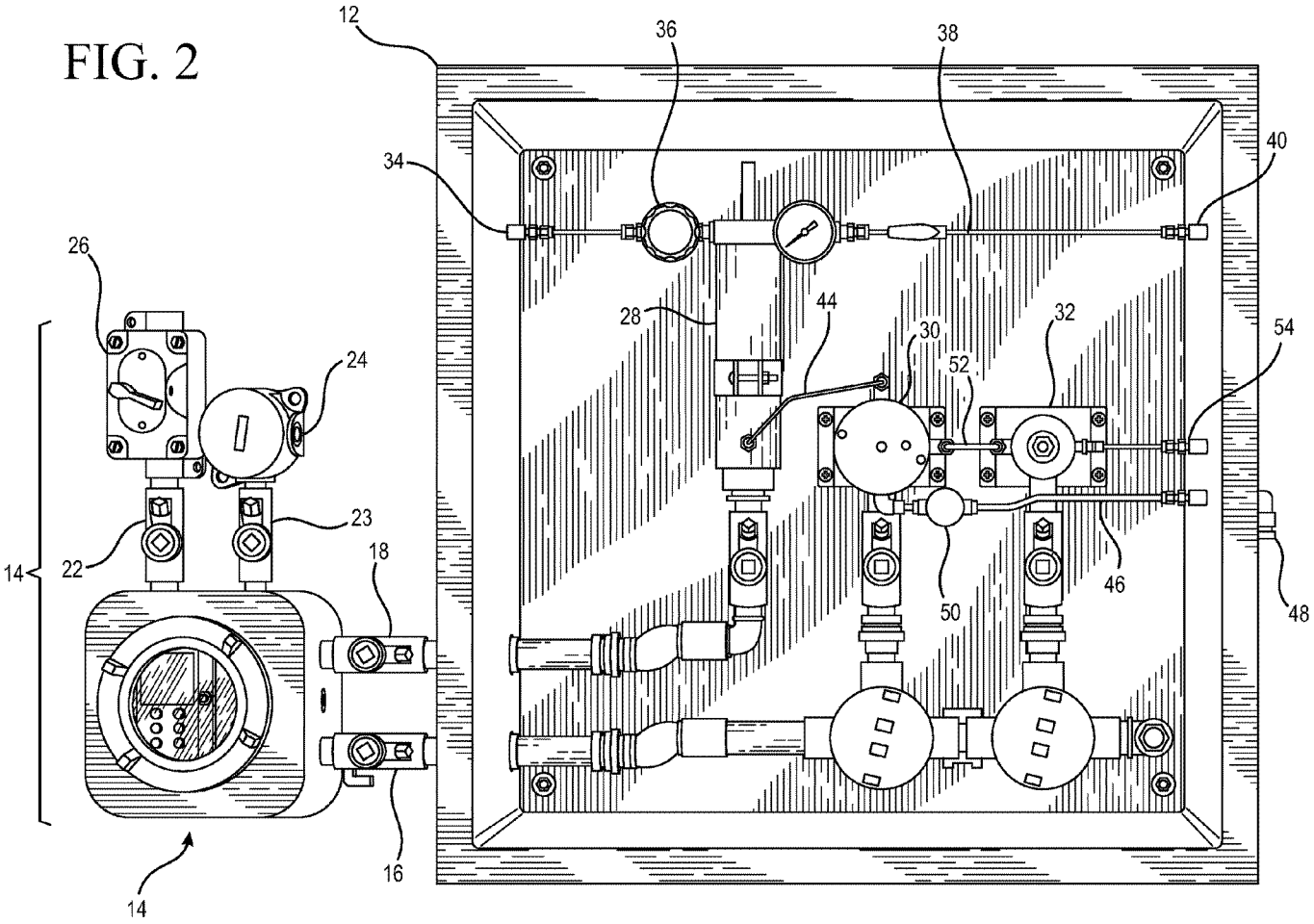
FIG. 2 is a front view of a vaporizer cabinet according to a physical construct of the invention.

FIG. 1 illustrates an embodiment of the inventive natural gas liquid vaporizer system 10. System 10 comprises a cabinet 12 preferably conforming in standards to a Class 1, Division 1 Group C, D, t3 (<200° C.) requirements. Disposed proximate to and exterior of the cabinet 12 is the power and communication assembly 14 connected through the cabinet side to its interior through secure sealed feedthrough conduits 16 and 18 comprising ¾ inch galvanized conduit. The construction of the feedthroughs conform to applicable NEC Sec. 500 (2011) Standard and generally constitute gasketed, conduit fittings threadably secured to the cabinet wall.

Figure 3:
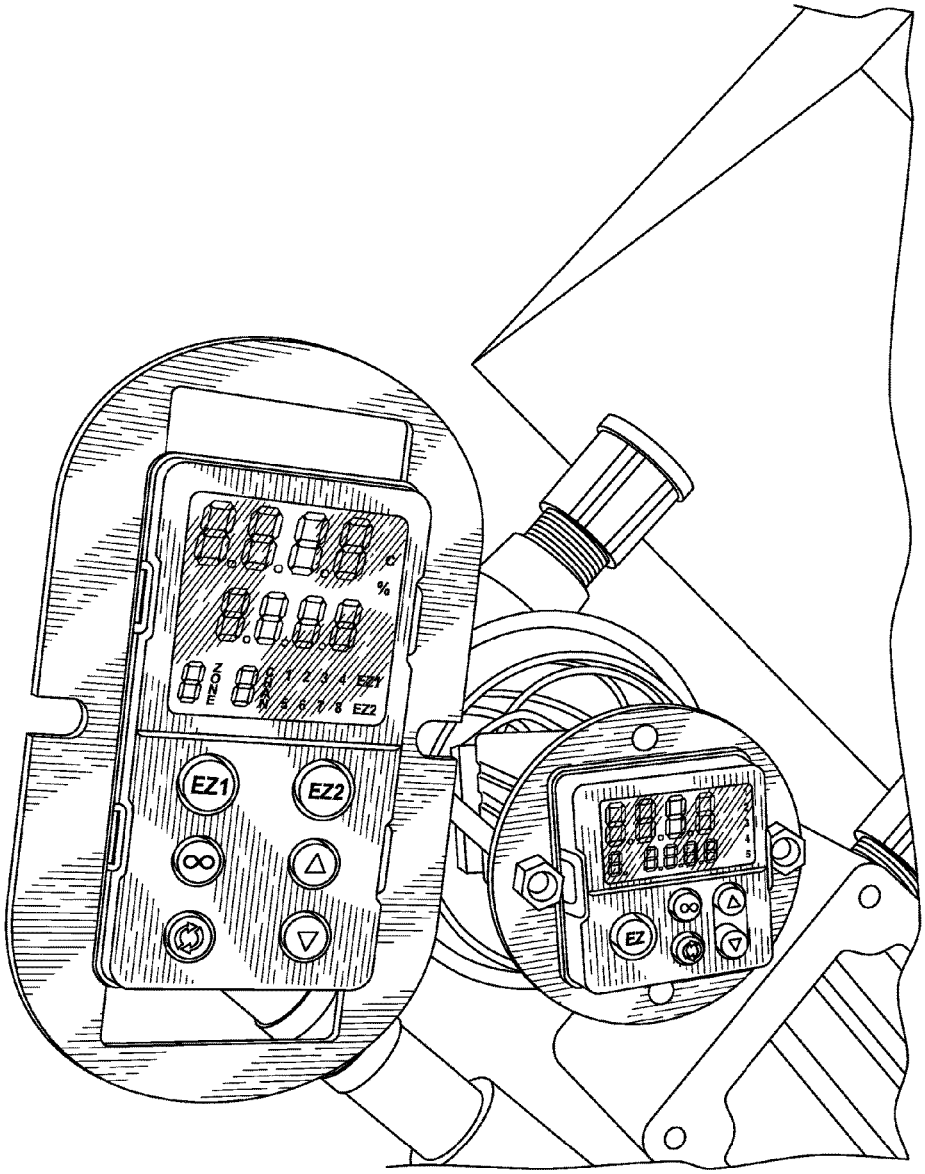
FIG. 3 is a front view of the flow circuit controllers employed in the depicted embodiment of the invention.
Figure 4:
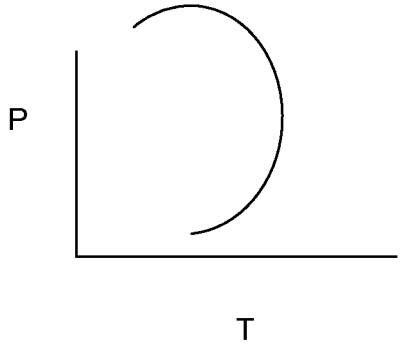
FIG. 4 is graphical representation of a pressure temperature curve of liquid natural gas.

A code-compliant electrical enclosure 20 connected to the cabinet through the feedthrough conduits 16 and 18 to the exterior of the cabinet 12, contains at least one temperature controller for the internal cabinet components described below. In this illustrated embodiment (also see FIG. 3), a Watlow Dual Controller (EZ-Zone) is encased within the electrical enclosure 20. Projecting from the top of the enclosure 20 are another pair of electrical conduits 22 and 23, respectively providing the main power to the system from a switch subassembly 26 and a digital communication connection 24. The communications connection preferably is hardwired and comprises a standard connection, e.g., RS 485 or USB but may also embody more modern wireless communication technology.

Referring to the interior of cabinet 12, as indicated above, it derives its power electrically and is connected via enclosure 20 via sealed feedthrough fittings 16 and 18. The electrical conduit secured by feedthrough conduit 18 is connected to a single path vaporizer 28 which itself is securely mounted within the insulated cabinet 12. The other electrical conduit, that secured by feedthrough conduit 16, is connected respectively to heated liquid block 30 and heated pressure regulator 32.

Turning to the gas sample pathway in respect to the cabinet 12 contemplated by the illustrated embodiment, the gas sample typically travels from its extraction point (i.e., a natural gas liquid line probe) through a small, sample gas line, generally consisting of small diameter stainless steel tubing connecting to a feedthrough 34 formed in the cabinet wall. Upon entry into the cabinet interior, the sample, typically at very high pressure, travels through the line to a first pressure reducing regulator 36 and then to heated liquid sample vaporizer 28. The junction of the vaporizer input includes a pressure remediating speed loop 38 or vent to prevent sample over pressurization during the vaporizing step. That speed loop/vent which may incorporate an intermediate one-way check valve, is connected to the cabinet exterior via feedthrough vent 40. Such a speed loop and its function are described in Assignee's earlier issued U.S. Pat. No. 7,484,404, the content of which is incorporated in its entirety herein by reference. The particular form, diaphragm or piston, of the regulator is selectable by a user for a particular installation. Notably, diaphragm regulators are believed to provide superior performance in the case of liquid sample streams.

In ordinary operation, the vaporized liquid sample passes from an exit orifice 42 proximate to the lower portion of the vaporizer 28 and travels via transport tube 44 to the liquid block 30, which in the illustrated embodiment is thermally conditioned by a 200 watt heater (not illustrated). Upon input at the upper portion of the liquid block, any liquids contained in the gas stream drop out an pass out of lower end of the liquid block 30 and into the cabinet interior and then to a sealed, drain-feedthrough 48 to exit the cabinet 12. To insure against any liquid back flow through drain pipe 46, it may be fitted with a one-way needle/check valve 50.

The vaporized liquid sample passes out of the liquid block via tube 52 to the further pressure reducing heated regulator 32. Having prevented dew point drop out/Joules-Thompson condensation of the vaporized sample stream by heating the sample during the pressure reduction, the sample stream has been properly condition for passage out of the cabinet via sample analyzer feedthrough 54.

The described system may include two discrete temperature controllers one associated with the vaporizer and the other with the regulator that, preferably are connected to communicate with a remote monitoring and control system allowing for changes to the system when deemed appropriate.

Although only a single embodiment of the invention has been illustrated in the forgoing specification, it is understood by those skilled in the art that many modifications and embodiments of the invention will come to mind to which the invention pertains, having benefit of the teaching presented in the foregoing description and associated drawing. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

I claim:

1. A natural gas liquid sample vaporizer system comprising:

a [vented] cabinet having a natural gas liquid sample input *configured to receive a natural gas liquid sample*, a pressure regulator *configured to reduce the pressure of the natural gas liquid sample*, a [single path] vaporizer *configured to vaporize the natural gas liquid sample output from the pressure regulator*, [a liquid block,]

a heated *pressure* regulator [and] *configured to reduce the pressure of the vaporized natural gas liquid sample,*

*a liquid drain configured to receive any unvaporized natural gas liquid,* a gas sample outlet, and a communications assembly electrically connected via appropriate secure feedthroughs to the cabinet, said assembly including an electrically powered temperature controller, an electrically powered communication outlet, and an electrical power input.

2. The natural gas liquid sample vaporizer system of claim 1 having a single gas sample path.

3. The natural gas liquid sample vaporizer system of claim 2 where the [liquid block] *heated pressure regulator* is heated by electrical power.

4. The natural gas liquid sample vaporizer system of claim 2 where the cabinet includes a speed loop for pressure control *and the liquid drain is located between the vaporizer and the heated pressure regulator*.

5. A method for conditioning a sample of natural gas liquid by reducing the liquid pressure and vaporizing the liquid extracted from a [high pressure] natural gas liquid line, comprising the steps of:

a) inputting a natural gas liquid sample into a sample conditioning system;

b) reducing the pressure of *the natural gas* liquid sample;

c) vaporizing the natural gas liquid sample;

d) passing [the vaporized natural gas liquid sample through a liquid block] *any unvaporized natural gas liquid remaining after vaporization through a liquid drain*; and e) passing the vaporized natural gas liquid sample through a pressure reducing regulator to a sample analyzer output while maintaining a sufficient temperature to prevent hydrocarbon dew point drop-out.

6. The method of claim 5 [where the liquid block is heated] *further comprising the step of passing the vaporized natural gas liquid sample through a liquid block before passing any remaining natural gas liquid through the liquid drain*.

7. The method of claim 5 where *the natural gas liquid is extracted from a high pressure line and where* the vaporized natural gas liquid is heated before and [after] *during* pressure reduction.

8. The method of claim 5 where the vaporized natural gas liquid sample follows a single gas sample path.

*9. A natural gas liquid sample vaporizer system comprising:*

*a cabinet having a natural gas liquid sample input configured to receive a natural gas liquid sample,*

*a pressure regulator configured to reduce the pressure of the natural gas liquid sample,*

*a single path vaporizer configured to vaporize the natural gas liquid sample output from the pressure regulator,*

*a heated pressure regulator configured to reduce the pressure of the vaporized natural gas liquid sample,*

*a liquid drain configured to receive any unvaporized natural gas liquid,*

*a gas sample outlet, and*

*a communications assembly electrically connected via appropriate secure feedthroughs to the cabinet, said assembly including an electrically powered temperature controller, an electrically powered communication outlet, and an electrical power input.*

*10. The natural gas liquid sample vaporizer system of claim 9 having a single gas sample path.*

*11. The natural gas liquid sample vaporizer system of claim 10 further including a liquid block disposed in the pathway between the vaporizer and heated pressure regulator.*

*12. The natural gas liquid sample vaporizer system of claim 10 where the cabinet includes a speed loop for pressure control.*

*13. A method for conditioning a sample of a liquid subject to Joule-Thompson condensation from a high pressure source by reducing the liquid pressure and vaporizing the extracted liquid, comprising the steps of:*

*a) inputting a natural gas liquid sample into a sample conditioning system;*

*b) reducing the pressure of the natural gas liquid sample input into the sample conditioning system;*

*c) vaporizing the natural gas liquid sample;*

*d) passing any unvaporized natural gas liquid remaining after vaporization through a liquid drain; and*

*e) passing the vaporized natural gas liquid sample through a pressure reducing regulator to a sample analyzer output while maintaining a sufficient temperature to prevent Joule-Thompson condensation.*

*14. The method of claim 13 further comprising the step of passing the vaporized natural gas liquid sample through a liquid block before passing any remaining natural gas liquid through the liquid drain.*

*15. The method of claim 13 where the vaporized liquid is heated before and during pressure reduction.*

*16. The natural gas liquid sample vaporizer system of claim 1 where the liquid drain is disposed in the pathway between the vaporizer and heated pressure regulator.*

*17. The natural gas liquid sample vaporizer system of claim 9 where the liquid drain is disposed in the pathway between the vaporizer and heated pressure regulator.*

*18. The natural gas liquid sample vaporizer system of claim 1 where the liquid drain outputs any unvaporized natural gas liquid remaining after vaporization.*

* * * * *